(12) United States Patent
Müller (10) Patent No.: US 6,677,358 B1
(45) Date of Patent: Jan. 13, 2004

(54) NIDDM REGIMEN

(75) Inventor: Peter Giørtz Müller, Princeton Junction, NJ (US)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/459,526

(22) Filed: Dec. 13, 1999

Related U.S. Application Data (63) Continuation of application No. PCT/DK98/00248, filed on Jun. 12, 1998.
(60) Provisional application No. 60/063,368, filed on Oct. 29, 1997.

(30) Foreign Application Priority Data

Jun. 13, 1997 (DK) .............................................. 0694/97

(51) Int. Cl.$^7$ .................. A61K 31/155; A61K 31/4453; A61K 31/451

(52) U.S. Cl. ..................................... 514/331; 514/635

(58) Field of Search ............................ 514/331, 635, 514/563

(56) References Cited

FOREIGN PATENT DOCUMENTS

EP         0 589 874 B1    9/1999

OTHER PUBLICATIONS

Moses et al., Diabetologia (40, Suppl. 1, A322) (Jun. 6, 1997) (abstract).*
Moses et al., Diabetes, vol. 46 (Suppl.1), pp. 93 (abstract), May 1, 1997.*
Dunning, B.E., Expert Opinion on Investigational Drugs, 6/8 (1041–1048) (abstract), 1997.*
J. Dyson et al Merrrill Lynch Report "Handling Investors Growth", Switzerland Pharmaceuticals, pp. 1–5 (Jun. 1996).
Kohei Kaku et al, "Possibility of the Appearance of New Antidiabetic Agents (1): Oral Antidiabetic Agents" Practice, vol. 13, No. 6, pp. 531–535 (1996) and English translation thereof.
N. Kondo., et al., Oral hypoglycemic agent/Insulin secretagogue/Non–sulfonylurea agent, Preclincal studies of AY4166, Japanese Journal of Clinical Studies ("Nippon Rinsho") vol. 55, Suppl. 2, pp. 159–163 (1995) and English translation thereof.
R.A. DeFronzo et al., "Efficacy of Metformin in Patients With Non–Insulin–Dependent Diabetes Mellitus", New England Journal of Medicine vol. 333., No. 9., pp. 541–549 (1995).
Organic–chemical drugs and their synonyms, 7. Aufl., 1994, Akademie Verlag GmbH, Berlin, pp. 1660 & 2483.
Pharmaceutisches Worterbuch, 8, Aufl., 1998, Walter de Gruyter Verlag, Berlin, Stichworterz: Medikamente & Arzneimittel., pp. A–III, A–VI & A–VII.

Deutches Arzneimittelbuch (DAB) 10, 1991, Stichwort: Tabletten, pp. 1–3.
Rechercheergebnis, Feb. 6, 2002.
J. Rachman et al., "Drugs on the Horizon For Treatment of Type 2 Diabetes" Diabetic Medicine., vol. 12., pp. 467–478 (1995).
R. Vigneri et al., "Treatment of NIDDM Patients with Secondary Failure To Glyburide: Comparison of the Addition of Either Meteformin or Bed–Time NPH Insulin to Glyburide" Diabetic & Metabolisme (Paris) vol. 17., pp. 232–234 (1991).
Ajinomoto et al., "Drugs of the Future", Prous Science Publishers. vol. 21 No. 6, Jun., 1995, pp. 610, Jun., 1996, pp. 639.
Francis L.S. Tse,et al., Effect of Food on the Bioavailability of SDZDJN608, an Oral Hypoglycemic Agent, from a Tablet and a Liquid–Filled Capsule in the Dog, Pharm, Research, vol. 13, pp. 440–444 (1996).
M. Hanefeld et al., "Rational Therapy of Type II Diabetes" vol. 53, pp. 914–924 (German language original and English translation thereof ) (1996).
J.D. yson et al., Abstract Dialog (R) Files 545: Novartis Company Report (Jun. 18, 1996).
Dunning, "New Non–Sulfonylurea Insulin Secratagogues" Exp. Opin. Invest. Drugs, 6: 1041–1048 (1997).
Hermann et al "Antihyperglycasmic Efficacy, Response Prediction and Dose–Response Relations of Treatment with Metformin and Sulphonylurea, Alone and in Primary Combination" Diabet. Med. 11:953–960 (1994).
Hirschberg, MS et al., Diabetes Care, vol. 23, pp. 349–353 (2000).
Horton et al., Diaeaz, vol. 49 (Supplement 1) , p. 1–A524 (2000).
A. Melander, Diabetic Medicine, vol. 13, pp. 143–147 (1996).
Wolffenbutte et al., European Journal of Clinical Pharmacology, vol. 45, pp. 113–116 (1993).
Ikenoue et al., British Journal of Pharmacology, vol. 120, pp. 137–145 (1997).
M. Kikuchi, Diabetic Medicine, vol. 13, pp. 151–155 (1996).
Ikenoue et al., Biol. Pharm. Bull., vol. 20, No. 4, pp. 354–359 (1997).

(List continued on next page.)

Primary Examiner—Phyllis G. Spivack
(74) Attorney, Agent, or Firm—Reza Green, Esq.; Richard N. Boak, Esq.; Marc A. Began, Esq.

(57) ABSTRACT

The present invention discloses a regimen for the treatment of type 2 diabetes, in which the endogenous secretion of insulin is stimulated in connection with meals, by administering a short-acting, oral hypoglycemic agent. Also, the present invention discloses a method of achieving improvement in glycemic control by combined use of repaglinide and metformin in NIDDM patients poorly controlled on metformin alone.

5 Claims, 4 Drawing Sheets

OTHER PUBLICATIONS von Nicolai et al., Arzneim.–Forsch./Drug Res., vol. 47, pp. 247–251 (1997).

Andrew D.B. Harraower, Clin. Pharmacokinet, vol. 31, pp. 111–119 (1996).

Antón–Fos et al., Arzneim.–Forsch./Drug Res., vol. 44, pp. 821–826 (1996).

S. Hu, European Journal of Pharmacology, vol. 442, 2002, pp. 163–171.

R.E. Pratley et al. Current Pharmaceutical Design, vol. 7(14), 2001,pp. 1375–1397.

M. Marre et al. Diabetes, Obesity and Metabolism, vol. 4,2002 pp. 177–186.

* cited by examiner

NIDDM REGIMEN

CROSS-REFERENCE TO RELATED APPLICATIONS

This application is a continuation of PCT/DK98/00248 filed on Jun. 12, 1998 and claims priority under 35 U.S.C. 119 of Danish application no. 0694/97 filed on Jun. 13, 1997 and U.S. provisional application No. 60/063,368 filed on Oct. 29, 1997, the contents of which are fully incorporated herein by reference.

FIELD OF THE INVENTION

The present invention relates to the use of a short-acting oral hypoglycemic agent and to a novel regimen in the treatment of type 2 diabetes in which the endogenous secretion of insulin is stimulated in connection with meals by administering in connection with the meals a short-acting oral hypoglycaemic agent. Also, the present invention relates to a method of achieving significantly improvement in the glycaemic control by a combined use of repaglinide and metformin in NIDDM patients poorly controlled on metformin alone.

BACKGROUND OF THE INVENTION

Diabetes is characterised by an impaired glucose metabolism manifesting itself among other things by an elevated blood glucose level in untreated diabetic patients. The underlying defects lead to a classification of diabetes into two major groups: type 1 diabetes, or insulin dependent diabetes mellitus (IDDM), which arises when patients lack β-cells producing insulin in their pancreatic glands, and type 2 diabetes, or non-insulin dependent diabetes mellitus (NIDDM), which occurs in patients with an impaired β-cell function besides a range of other abnormalities.

Type 1 diabetic patients are currently treated with insulin, while the majority of type 2 diabetic patients are treated either with agents that stimulate β-cell function or with agents that enhance the tissue sensitivity of the patients towards insulin. Since the agents that stimulate β-cell function or enhance the tissue sensitivity of the patients towards insulin are typically administered orally, these agents are collectively referred to as oral hypoglycemic agents or OHAs.

Among the agents applied for stimulation of the β-cell function, those acting on the ATP-dependent potassium channel of β-cells are most widely used in current therapy. The so-called sulphonylureas such as tolbutamide, glibenclamide, glipizide, and gliclazide are used extensively and other agents such as repaglinide also acting at this molecular site are under development. Repaglinide is (S)-(+)-2-ethoxy-4-[2-[[3-methyl-1-[2-(1-piperidinyl)phenyl]butyl]amino]-2-oxo-ethyl]benzoic acid, a compound described i.a. in European patent application publication No. 0 589 874 (to Dr. Karl Thomae GmbH). Among the agents applied to enhance tissue sensitivity towards insulin, metformin is a representative example.

Even though sulphonylureas are widely used in the treatment of NIDDM this therapy is, in most instances, not satisfactory: In a large number of NIDDM patients sulphonylureas do not suffice to normalise blood sugar levels and the patients are, therefore, at high risk for acquiring diabetic complications. Also, many patients gradually lose the ability to respond to treatment with sulphonylureas and are thus gradually forced into insulin treatment. This shift of patients from oral hypoglycaemic agents to insulin therapy is usually ascribed to exhaustion of the β-cells in NIDDM patients.

Over the years, numerous attempts have therefore been made to provide novel agents which stimulate β-cell function in order to offer the NIDDM patients an improved treatment.

SUMMARY OF THE INVENTION

In one preferred aspect, the present invention relates to the use of a short-acting hypoglycemic agent capable of stimulating insulin secretion from β-cells for the manufacture of a medicament adapted to stimulate prandial insulin secretion for the treatment of postprandial hyperglycemia in NIDDM.

In another preferred aspect, the present invention relates to the use of repaglinide for the manufacture of a medicament adapted to stimulate prandial insulin secretion for the treatment of postprandial hyperglycemia in NIDDM.

In another preferred aspect, the present invention relates to the use of A-4166 for the manufacture of a medicament adapted to stimulate prandial insulin secretion for the treatment of postprandial hyperglycemia in NIDDM (A4166 is N-[(trans-4-isopropylcyclohexyl)carbonyl]-D-phenylalanine (Shinkai H et al. J Med Chem 32: 1436–1441)).

In another preferred aspect, the present invention relates to the use of gliquidone for the manufacture of a medicament adapted to stimulate prandial insulin secretion for the treatment of postprandial hyperglycemia in NIDDM.

In another preferred aspect, the present invention relates to a method of treating NIDDM which comprises stimulating the insulin secretion in connection with a meal by administering prandially to a patient in need of such a treatment an effective amount of a short-acting hypoglycemic agent.

In another preferred aspect, the present invention relates to a method of treating NIDDM which comprises stimulating the insulin secretion in connection with a meal by administering prandially to a patient in need of such a treatment an effective amount of repaglinide.

In another preferred aspect, the present invention relates to a method of treating NIDDM which comprises stimulating the insulin secretion in connection with a meal by administering prandially to a patient in need of such a treatment an effective amount of A-4166.

In another preferred aspect, the present invention relates to a method of treating NIDDM which comprises stimulating the insulin secretion in connection with a meal by administering prandially to a patient in need of such a treatment an effective amount of gliquidone.

In another preferred aspect, the present invention relates to a pharmaceutical kit suitable for use in achieving improved glycaemic control in NIDDM patients, the kit comprising an amount of repaglinide formulated for administration to a NIDDM patient; and a synergistically effective amount of metformin, formulated for administration to the NIDDM patient.

In a further preferred aspect, the present invention relates to a method of treating NIDDM which comprises stimulating the insulin secretion in connection with a meal by administering prandially to a patient in need of such a treatment an effective amount of a short-acting hypoglycemic agent supplemented with administration of a long-acting hypoglycemic agent. The long-acting hypoglycemic agent can be administered once per day or divided in sub-doses, preferably two or three sub-doses. Such a regimen may be useful in cases where the patient's basal insulin level is lower than desirable. A preferred short-acting hypoglycemic agent for use in such a regimen is selected from the group comprising repaglinide, gliquidone and A-4166. A preferred long-acting hypoglycemic agent for use in such a regimen is selected from the group comprising metformin, chlorpropamide, tolbutamide, glibenclamide, glibornuride, gliclazide, glipizide and troglitazone.

Surprisingly, it has been found that when repaglinide is administered together with metformin to NIDDM patients whose glycemic control is poor on metformin alone a significant improvement in the glycaemic control is observed. More particularly, it has been found that there is a synergism between repaglinide and metformin. Thus, in a further preferred aspect, the present invention relates to a method of achieving improved glycemic control in NIDDM patients which comprises administering to a patient in need of such a treatment, an effective amount of repaglinide in a regimen which further comprises treatment with metformin.

In a further preferred aspect, the present invention relates to a pharmaceutical composition which comprises repaglinide and metformin together with a suitable carrier. In one preferred aspect, such a pharmaceutical composition is provided in the form of a tablet. In another preferred aspect, such a pharmaceutical composition is provided in the form of a capsule. Said composition preferably contains from about 0.01 mg to about 8 mg of repaglinide, more preferred from about 0.5 mg to about 6 mg of repaglinide and from about 50 mg to about 1500 mg, preferably from about 100 mg to about 1200 mg of metformin per dose unit.

In the present text, the term "a short-acting hypoglycemic agent" is used to designate a hypoglycemic agent with which maximum secretion of insulin is attained within 1 hour, preferably within 30 min. after administration of the agent, most preferred within 20 min. and which furthermore has a biological half-life, $T_{1/2}$, of less than 2 hours, preferably less than 1.5 hours. The term "a long-acting hypoglycemic agent" is used to designate a hypoglycemic agent with which maximum secretion of insulin is attained more than 1 hour after administration of the agent.

BRIEF DESCRIPTION OF THE DRAWINGS

The present invention is further illustrated with reference to the drawings wherein.

DETAILED DESCRIPTION OF THE INVENTION

Healthy persons have a 24 hour basal secretion of insulin. In connection with meals there is an increased demand for insulin and via a complex feed-back mechanism the pancreas is stimulated to fulfil the demand. After a while, the insulin level again decreases to the basal level.

For the first many years of the disease, dietary restrictions may help NIDDM patients to compensate for the earliest manifestation of their disease which is the decreasing ability of their pancreas to secrete the amount of insulin required in order to control the post prandial blood glucose. At a more progressed state of the disease, also the basal insulin secretion becomes insufficient. When medical treatment becomes necessary, an oral hypoglycemic agent will often be prescribed.

Most of the oral hypoglycemic agents presently in use have a fairly long biological half-life. This implies that when they are administered two or three times per day, which is usually the case, the insulin level will almost constantly be higher than corresponding to the basal level. On the other hand, the peak levels of insulin seen in healthy persons in connection with meals will not be achieved. Such a regimen has certain disadvantages. Thus, it is believed that the diabetic late complications are closely related to a less than optimal glycaemic control caused by, for example, a fairly constantly increased insulin level. Another disadvantage with the long-acting hypoglycemic agents is that they to a very high degree dictate the life-style of the patient: once the patient has taken a long-acting hypoglycemic agent he has only little freedom to deviate from his dietary plan.

The regimen according to the present invention makes it possible for NIDDM patients to mimic the variations in the insulin level seen in healthy persons. Thus, if a patient has a satisfactory basal insulin level, the extra insulin needed in connection with a meal can be secreted by a short stimulation of the pancreas in connection with the meal. Since a short-acting hypoglycemic agent is rapidly absorbed, it can be taken in connection with the meal, preferably shortly before or at the beginning of the meal, optionally during the meal or even shortly after. The resulting stimulation of the pancreas will produce a peak in the insulin level just when it is needed and due to the short half-life of the short-acting hypoglycemic agent, the insulin level will soon go down to the basal level again. The regimen according to the present invention makes it permissible for a NIDDM patient, to a certain degree, to act on an impulse as regards meals and thus adds to the patient's quality of life.

The designation "meal" as used in the present text is intended to mean breakfast, lunch dinner or midnight snack.

When the expression "meal-related" is used in the present text in connection with the administration of a short-acting hypoglycemic agent it preferably designates that the short-acting hypoglycemic agent is administered shortly before or at the beginning of the meal. However, the administration can obviously also take place during the meal or even shortly after without deviating from the idea behind the invention. Thus, the expression "meal-related" preferably means from about 10 minutes before the meal starts to about 10 minutes after the meal is finished, more preferred from about 5 minutes before the meal starts until the meal is finished, most preferred at the beginning of the meal.

If a NIDDM patient does not produce enough insulin to provide a satisfactory basal insulin level, the meal-related administration of a short-acting hypoglycemic agent can be supplemented with the administration of a long-acting hypoglycemic agent. Typically, a long-acting hypoglycemic agent will be administered once, twice or three times per day. Thus, in cases where there is a need to supplement the meal-related administration of a short-acting hypoglycemic agent with a long-acting one, the long-acting one can either be administered at separate hours or together with the short-acting one, optionally in the same tablet or capsule. The advantage of a combined administration is that it is likely to give an improved compliance with the prescribed regimen.

One advantage which can be expected from the regimen according to the present invention is that it, due to its simplicity, will improve the patients' compliance.

Another advantage is that no long-time planning of meals is needed: if the patient has an extra meal he takes an extra tablet, if he skips a meal, he takes no tablet.

A further advantage which can be expected from this regimen is that the patients will have fewer serious diabetic late complications.

Repaglinide is a short-acting hypoglycemic agent with a short half-life. Examples of other short-acting hypoglycemic agents with a short half-lives are gliquidone and A-4166.

Examples of long-acting hypoglycemic agents are biguanides such as metformin and sulphonylureas such as chlorpropamide, tolbutamide, glibenclamide, glibornuride, gliclazide and glipizide. A further example of a long-acting hypoglycaemic agent is troglitazone.

The particular hypoglycemic agent or agents to be used and the optimal dose level for any patient will depend on a variety of factors including the efficacy of the specific agent employed, the age, body weight, physical activity, and diet of the patient, on a possible combination with other drugs, and on the severity of the case. It is recommended that the dosage of the hypoglycemic agent or agents of this invention be determined for each individual patient by those skilled in the art.

When repaglinide is given—either alone or in combination with a biguanide or a sulphonylurea or another type of OHA—the amount of repaglinide is preferably in the range of from 0.01 mg to 6 mg, more preferred in the range of from 0.2 mg to 5 mg per meal.

When metformin is given in combination with repaglinide, the daily dosage is preferably in the range of from 200 mg to 3000 mg per day.

The present invention is further illustrated by the following examples which, however, are not to be construed as limiting the scope of protection. The features disclosed in the foregoing description and in the following examples may, both separately and in any combination thereof, be material for realizing the invention in diverse forms thereof.

EXAMPLES

Example 1
Repaglinide can be Given in a Flexible Dosing Regimen to Patients with Type 2 Diabetes As evidenced by the present study, the short duration of action ($T_{1/2}$=one hour) makes repaglinide suitable for a meal-related dosing regimen and provides a more flexible everyday life for people with diabetes.

In a single-centre, randomised, open-label, parallel group comparison study it was investigated whether repaglinide given preprandially will maintain glycaemic control in patients who skip a meal (lunch) or have an extra meal (bedtime snack) [mixed regimen] as compared with those who have three regular meals [fixed regimen].

A total of 25 diet-treated patients with type 2 diabetes were enrolled (18 men and 7 women) and given a fixed 1 mg dose of repaglinide preprandially (therapeutic dose range: 0.5–4 mg). After one week of stabilisation patients were randomised to the mixed or fixed regimen for a period of 21 days if blood glucose was >140 mg/dl.

Mean fructosamine values decreased (p<0.05) in both groups (fixed: 3.10 to 2.68 mmol/l; mixed: 3.37 to 2.85 mmol/l) with no significant difference between regimen groups. Mean fasting blood glucose (FBG) showed no statistically significant differences between the fixed and mixed groups. Mean FBG decreased to approximately 120 mg/dl in both groups and the difference was not statistically significant. Based on a 37-point blood glucose profile, AUC over 24 hours was not statistically significant between the fixed and mixed groups. When lunch was omitted, blood glucose levels remained stable until next meal. Both dose regimens were well tolerated and no hypoglycaemic episodes or serious adverse events were reported.

Thus, this study demonstrates that patients who occasionally deviate from the recommended meal plan may add an extra meal or skip one, taking repaglinide only when they have a meal, and still maintain their glycaemic control without adverse effect.

Example 2
Improved Glycaemic Control with Repaglinide in NIDDM with 3 Times Daily Meal Related Dosing Abstract Repaglinide belongs to a new chemical class of insulin secretagogues and is a short-acting and rapid acting insulin releaser. The potential impact of tailoring insulin release to meal in-take was investigated in a study comparing 3 times daily dosing with repaglinide just before meals to the same dosage administered twice daily. Eighteen OHA-naive NIDDM patients entered a 4-week, single centre, double-blind study, and were randomised to either 0.25 mg repaglinide before breakfast, lunch and dinner (REP3), or 0.5 mg before breakfast, placebo at lunch, and 0.25 mg before dinner (REP2). After two weeks the doses were doubled. At baseline, blood glucose, insulin, and C-peptide profiles were identical between the two groups. After 4 weeks, fasting blood glucose had decreased significantly in both groups (REP2: 11.2 to 9.6 mmol/l and REP3: 11.2 to 8.4 mmol/l). The overall glycaemic control was better in REP3 when compared with REP2, as blood glucose ($AUC_{0-24\ h}$) was 8.91 mmol/l in REP2 and 7.00 mmol/l in REP3 (P<0.05). The same significant difference was also found with glucose AUC (0–16 h). This difference in improvement of glycaemic control was reflected in a significant decrease in $HbA_{1c}$ levels in REP3, from 7.5 to 6.5% (P<0.05), while $HbA_{1c}$ decreased non-significantly in REP2 (from 7.1 to 6.8%). In both groups plasma insulin decreased to pre-treatment levels before the next meal and there was no increase in plasma insulin during the night time in comparison with pre-treatment levels.

In summary, repaglinide treatment caused significant improvement in glycaemic control in OHA-naive NIDDM patients and administration of the same total daily repaglinide dose showed additional advantages in regard to glycaemic control when given before the three main meals as compared to 2 times daily. At the same time it was possible to avoid both between meals and nocturnal hyperinsulinemia.

Introduction

Repaglinide is a novel insulin secretagogue, which acts on the ATP-sensitive potassium channel in pancreatic β-cells, but binds to a different site from sulphonylureas. Repaglinide has been developed for the treatment of patients with NIDDM whose blood glucose is not adequately controlled by diet alone. Because repaglinide is rapidly absorbed from the gastrointestinal tract and has a short plasma half-life, it is well suited for meal-related administration. The present study was designed to investigate the effects on glycaemic control of repaglinide when given at the same daily dose either morning and evening or preprandially at the three main meals.

Methods

This was a double-blind, placebo-controlled study involving patients with NIDDM, aged 40 to 70 years, with a body mass index >25 kg/m$^2$, fasting blood glucose (FBG) between 6.5 and 13 mmol/l, $HbA_{1c}$<11% and fasting C-peptide >0.3 pmol/ml. Of 18 patients enrolled, 17 were randomised to 4 weeks treatment with either 0.25 mg repaglinide three times daily before the three main meals (REP3), or 0.5 mg repaglinide before breakfast, placebo before lunch and 0.25 mg before dinner (REP2). After 2 weeks, the doses were doubled to 0.5 mg before each meal (REP3) and 1 mg+0.5 mg (REP2). Each patient was seen at three visits during the 4-week study period. A 24-hour hormonal and metabolic profile was examined at baseline and day 28.

Results

Eight patients in the REP3 group and 9 patients in the REP2 group completed the study.

Glycemic Control

Figure 1:
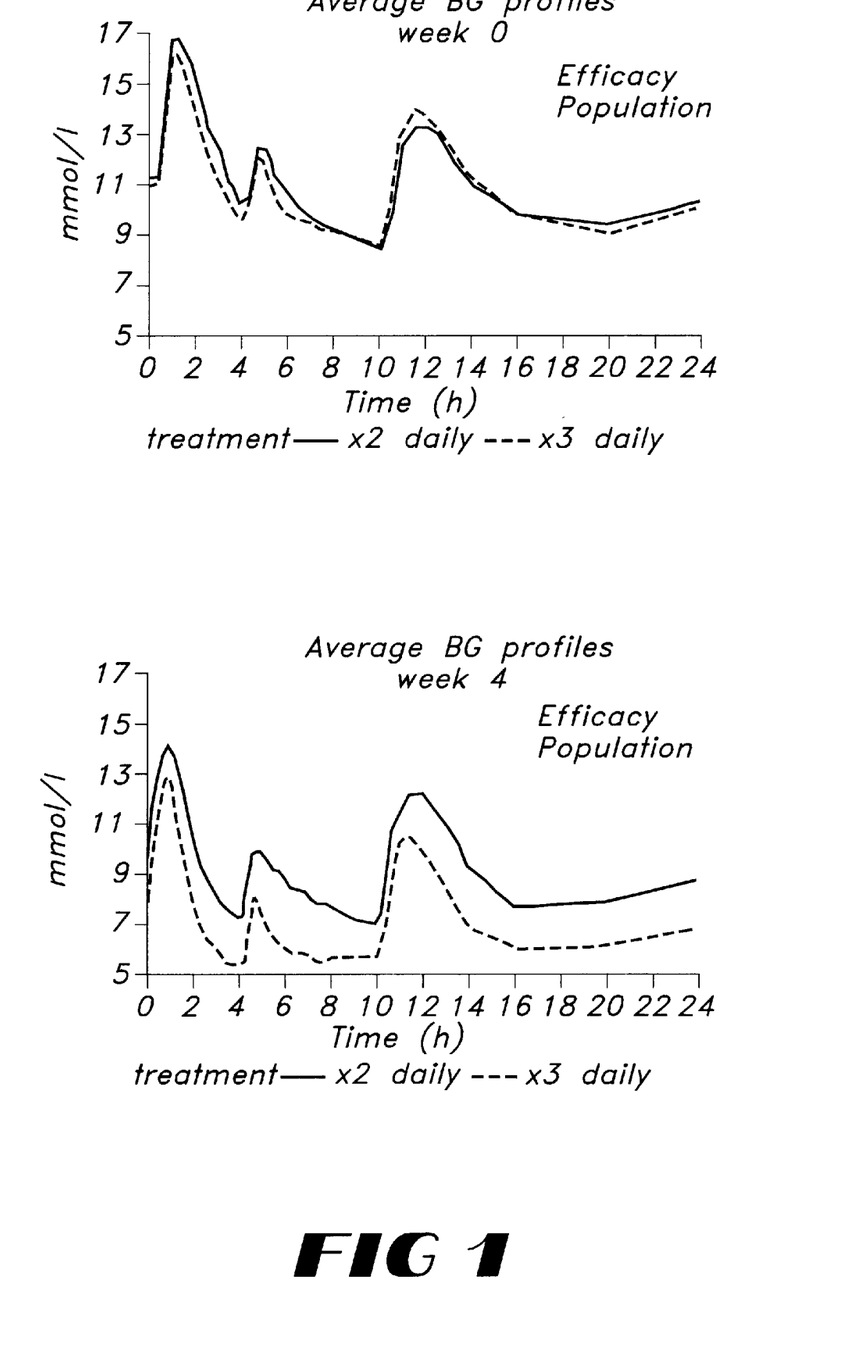
FIG. 1 shows mean blood glucose profiles at baseline and week 4.

After 4 weeks of treatment, blood glucose had decreased in both the REP3 and REP2 groups (P<0.01) (FIG. 1). However, preprandial blood glucose values were 1 to 2 mmol/l lower with REP3 than with REP2, and postprandial values were significantly lower, by about 2.5 mmol/l (P<0.05).

Mean FBG (±SEM) decreased significantly in both groups (P<0.001). In the REP3 group, the decrease was from 11.1±1.24 mmol/l to 8.4±1.01 mmol/l, whilst in the REP2 group, the decrease was from 11.3±0.73 mmol/l to 9.6±0.7 mmol/l. $HbA_{1c}$ (±SEM) also decreased in both groups after 4 weeks of treatment (REP3: 7.51±0.78% vs 6.51±0.64%; REP2: 7.12±0.24% vs 6.84±0.34%), but the decrease was only statistically significant in the REP3 group (P=0.004).

Figure 2:
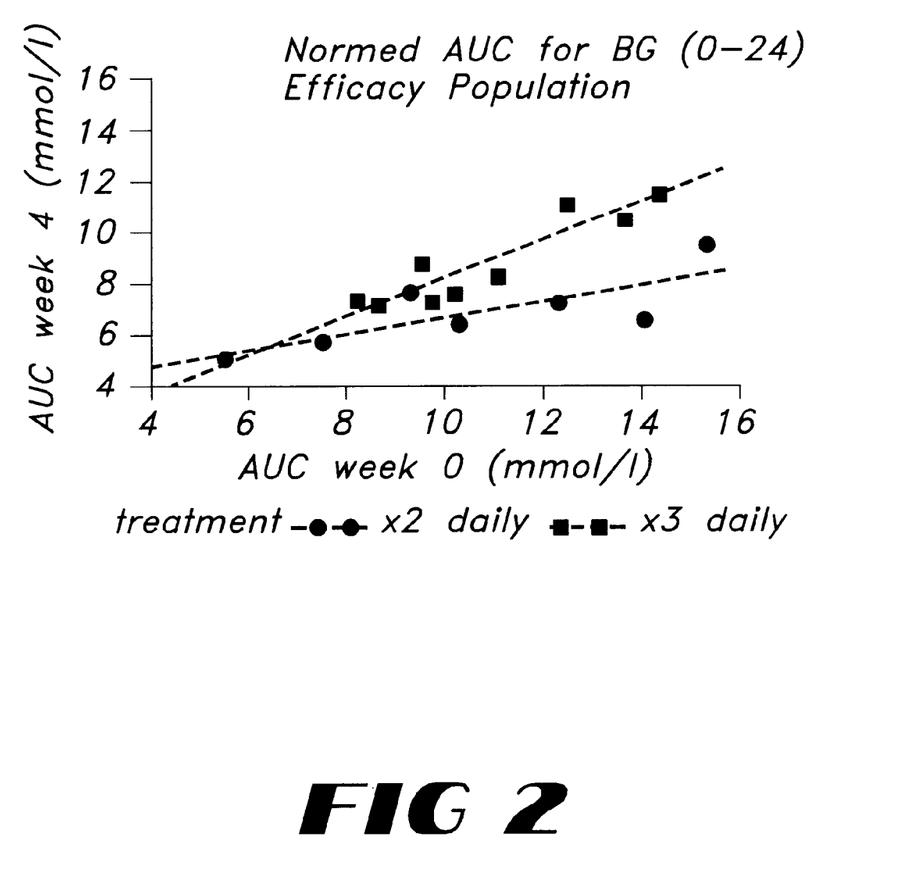
FIG. 2 shows normed AUC for blood glucose (0–24) after 4 weeks versus normed AUC for blood glucose (0–24) at baseline.

When $AUC_{0-24\ h}$ for glucose after 4 weeks of treatment was plotted versus $AUC_{0-24\ h}$ for glucose at baseline (FIG. 2), the slope estimates for the REP3 and REP2 groups differed significantly from one another (P<0.04). A similar trend towards greater glycaemic control with REP3 than with REP2 was observed for $AUC_{0-16\ h}$, though the difference between the groups only just reached statistical significance.

Circulating Insulin and C-Peptide

Figure 3:
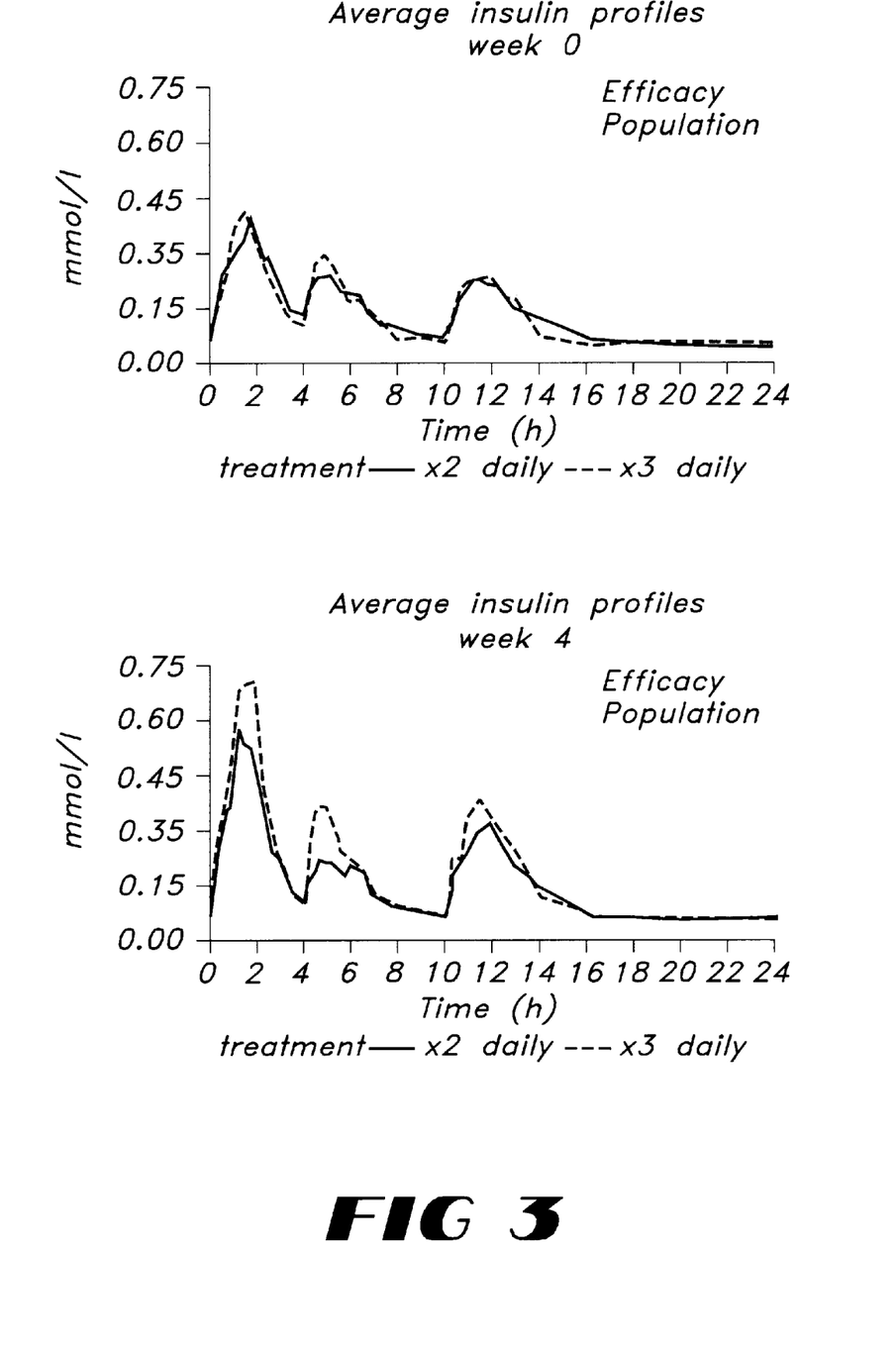
FIG. 3 shows mean plasma insulin profiles at baseline and week 4.

There were no significant differences between the REP3 and REP2 groups in preprandial or postprandial plasma insulin or plasma C-peptide values during the study. Normed $AUC_{0-24\ h}$ for plasma C-peptide increased in both groups after 4 weeks of treatment. Normed $AUC_{0-24\ h}$ for plasma insulin increased by 20% in the REP2 group and 35–40% in the REP3 group (FIG. 3), but the difference was not significant. In both treatment groups, plasma insulin decreased to pre-treatment levels before the next meal, and there was no increase in plasma insulin during the night in comparison with pre-treatment levels.

Plasma Repaglinide

The pharmacokinetic profile of repaglinide was characterised by a high peak value in the morning in the REP2 group, and a high peak in the afternoon in the REP3 group. However, the mean $AUC_{0-9\ h}$ and $AUC_{0-24\ h}$ for repaglinide were similar in both groups, showing that both groups received matching total daily drug exposure.

Safety Results

No serious adverse events were reported in either treatment group. The only non-serious adverse events were mild hypoglycemic episodes and one case of influenza Conclusions Repaglinide produced a significant improvement in glycaemic control in NIDDM patients, with only mild adverse events at the dose levels used. While the two treatment regimens (twice daily and three times daily preprandially) had similar insulin secretion rates, and did not cause 24-hour hyperinsulinemia, the data indicate that greater metabolic control is achieved when repaglinide is dosed prior to the three major meals as compared to before just breakfast and dinner.

Example 3

Additional Treatment with Repaglinide Provides Significant Improvement in Glycemic Control in NIDDM Patients Poorly Controlled on Metformin Abstract This multi centre, randomised trial was designed to compare the effect on glycaemic control of repaglinide (REP) in combination with metformin (MET) against monotherapy with either drug in NIDDM patients inadequately controlled on MET alone (mean $HbA_{1c}$: 8.5%). Eighty three patients were included in this three-armed, double-blind, double-dummy parallel group study. After a 4–5 week run-in period on their usual dose of MET, patients were randomized to either REP or MET monotherapy, or REP+MET combination therapy. The MET dose was kept constant throughout the study (1–3 g/day). The REP dose was determined during a 4–8 week titration phase (initial REP dose: 0.5 mg three times a day before meals; maximum dose: 4 mg three times a day before meals). A 3-month maintenance period followed the titration phase. From the baseline to final visit, combination therapy with MET+REP significantly (P<0.005) improved glycemic control compared with REP or MET monotherapy (mean change in $HbA_{1c}$: −1.41% (MET+REP), −0.38% (REP), −0.33% (MET); mean change in fasting blood glucose (mmol/l): −2.18 (MET+REP), 0.49 (REP), −0.25 (MET). No statistical differences were seen between the two monotherapies and MET+REP combination therapy with respect to fasting insulin and C-peptide levels, and lipid profiles. MET and MET+REP treatment caused more gastrointestinal side effects than REP treatment. No severe hypoglycemic events were observed in any group. In conclusion, REP treatment provided the same glycemic control as MET with less gastrointestinal side effects. REP+MET therapy induced significant improvements in metabolic control in contrast to either REP or MET, bringing $HbA_{1c}$ down into the range of acceptable control. The data also suggest that the combination of REP and MET may have synergistic properties in this type of patient.

Introduction

Repaglinide (REP) is a novel oral hypoglycemic agent which has been developed for the treatment of patients with NIDDM whose blood glucose is not controlled by dietary measures alone. The drug is rapidly absorbed, has a short plasma half-life, binds to a different site from sulfonylureas on the ATP-sensitive potassium channel on pancreatic β-cells, and is excreted via the bile. Repaglinide (REP) stimulates an insulin release profile similar to the physiological postprandial state. As metformin (MET) and REP have complementary mechanisms of action, the aim of the present study was to investigate the efficacy and safety of REP as combination therapy with MET in patients inadequately treated with MET alone.

Methods

This study was a randomised, double-blind, parallel group trial performed at 9 centres in Australia. Eighty-three patients with NIDDM, aged 40–75 years, a body mass index of >21 kg/$M^2$, and inadequately controlled ($HbA_{1c}$>7.1%) after more than 6 months of MET treatment were enrolled. After a 4–5 week open baseline period of MET treatment, patients were randomised either to continue on MET at their usual dose (1–3 mg/day) or to treatment with a combination of MET and REP or REP alone. The dose of REP was determined during a 4–8 week titration period (initial dose 0.5 mg three times daily preprandially (three times a day before meals), maximum dose 4.0 mg three times a day before meals). The dose reached at the last titration step was continued during a 3-month maintenance period. The patients were seen at eight scheduled visits.

Results

A total of 83 patients were enrolled in the trial (MET+REP: 27; REP: 29; MET: 27), of whom 74 completed the study (MET+REP: 27; REP: 26; MET: 21).

Glycemic Control and Metabolic Indices

Figure 4:
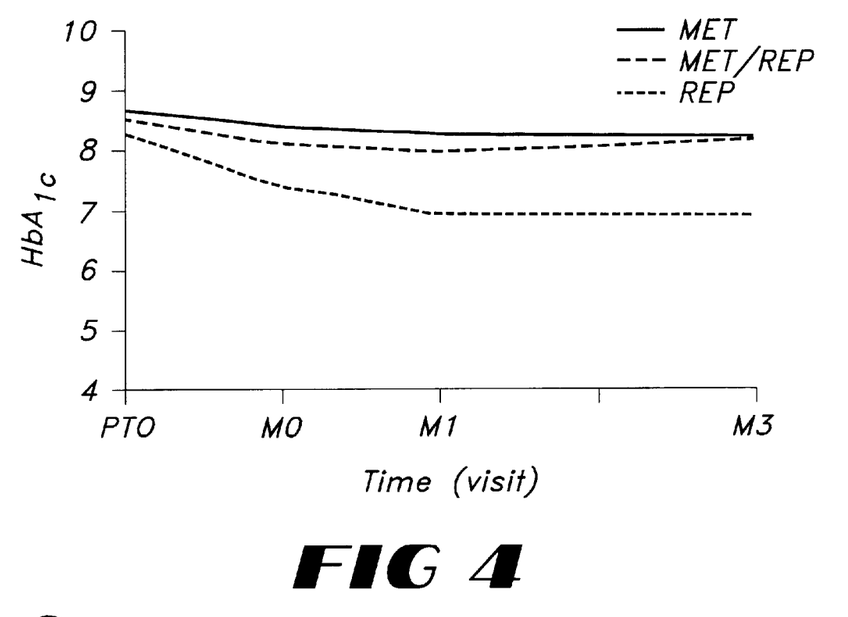
FIG. 4 shows changes in $HbA_{1c}$ during the titration (PTO-MO) and maintenance (MO-M3) treatment periods.
Figure 5:
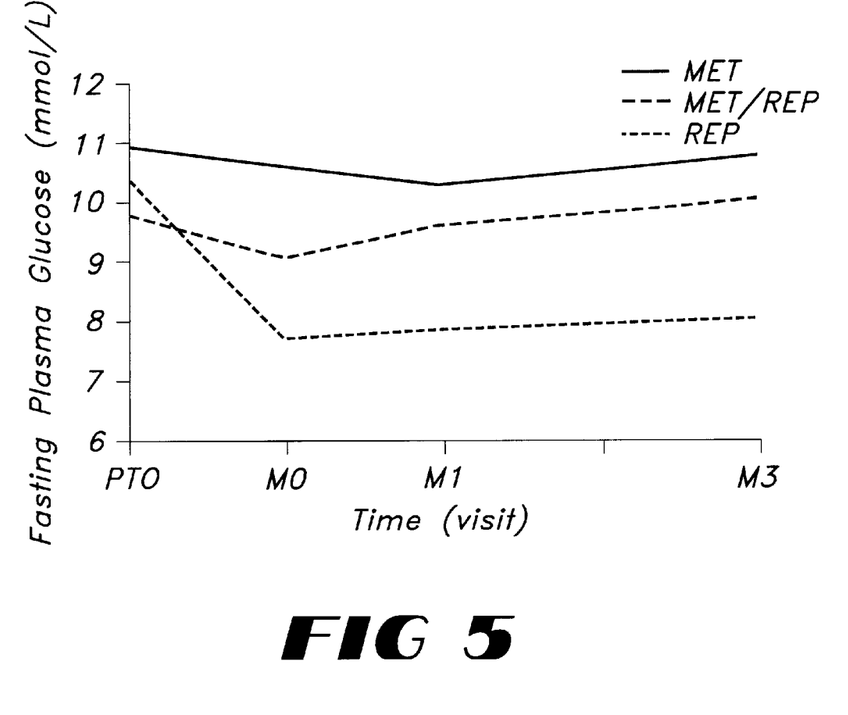
FIG. 5 shows changes in fasting plasma glucose during the titration (PTO-MO) and maintenance (MO-M3) treatment periods.

For patients in the MET+REP group, mean $HbA_{1c}$ and fasting plasma glucose (FPG) decreased significantly from 8.32 to 6.91% (p P<0.005) and from 10.22 to 8.04 mmol/l (P<0.005), respectively between baseline and the final visit (FIGS. 4 and 5). There were no significant changes in either parameter for the MET and REP groups (Table 1).

Fasting insulin and C peptide levels increased significantly during the study in the MET+REP and REP groups (P<0.05), but not in the MET group (Table 2).

Patients in the REP group had a small but statistically significant increase in total, HDL- and LDL-cholesterol levels during the study (P<0.05). HDL-cholesterol also increased in the MET group (P<0.05) (Table 3).

Safety Evaluation

A total of 339 adverse events were reported, of which 27 were considered probably or possibly related to study drug.

The frequency of drug-related adverse events was higher in the MET+REP group (59.3%) than in the monotherapy groups (REP: 25.0%; MET: 14.8%). MET+REP and MET treatment caused more gastrointestinal side effects than REP treatment (MET+REP: 14.8%; MET: 7.4%; REP: 3.6%). There were no statistically significant differences between the treatment groups in laboratory tests or vital signs.

Nine patients (33.3%) in the MET+REP group reported hypoglycemic episodes, compared to 3 (17.9%) in the REP group and none in the MET group. None of the hypoglycemic episodes were severe. One third of the patients with hypoglycemic episodes had these in the titration phase. One patient in the MET+REP group recorded 12 of the 30 episodes reported.

During the study, the mean body weight increased in the MET+REP group (+2.4±0.5 kg, P<0.05) and REP group (+2.98±0.49 kg, P<0.05), but decreased in the MET group (−0.86±0.51 kg, NS). The difference between the MET+REP and MET groups was statistically significant (P<0.05).

TABLE 1

Mean change in $HbA_{1c}$ (%) and fasting plasma glucose (FPG) from baseline to the end of the 3-month maintenance period.

| | Change in $HbA_{1c}$ (%) | 95% C.I. | Change in FPG (mmol/l) | 95% C.I. |
|---|---|---|---|---|
| Metformin/ repaglinide | −1.41 ± 0.23 | [−1.87; −0.95]* | −2.18 ± 0.45 | [−3.07; −1.28]* |
| Repaglinide | −0.38 ± 0.23 | [−0.84; 0.08] | 0.49 ± 0.47 | [−0.44; 1.42] |
| Metformin | −0.33 ± 0.24 | [−0.80; 0.15] | −0.25 ± 0.47 | [−1.18; 0.68] |
| Metformin/ repaglinide vs repaglinide | −1.03 ± 0.32 | [−1.78; −0.29]* | −2.66 ± 0.65 | [−4.14; −1.18]* |
| Metformin/ repaglinide vs metformin | −1.08 ± 0.33 | [−1.84; −0.33]* | −1.92 ± 0.65 | [−3.40; −0.44]* |

Data are means ± SEM. *P < 0.05

TABLE 2

Mean change in fasting insulin and C peptide from baseline to the end of the maintenance treatment period.

| Treatment groups | Change in fasting insulin (mU/l) | 95% C.I. | Change in C peptide (nmol/l) | 95% C.I. |
|---|---|---|---|---|
| Metformin/ repaglinide | 4.23 ± 1.50 | [1.24; 7.23]* | 0.17 ± 0.07 | [0.03; 0.30]* |
| Repaglinide | 4.04 ± 1.56 | [0.93; 7.16]* | 0.18 ± 0.07 | [0.03; 0.30]* |
| Metformin | 1.05 ± 1.60 | [−2.13; 4.23] | 0.02 ± 0.07 | [−0.13; 0.16] |
| Metformin/ repaglinide vs repaglinide | 0.19 ± 2.17 | [4.78; 5.15] | −0.01 ± 0.10 | [−0.24; 0.21] |
| Metformin/ repaglinide vs metformin | 3.18 ± 2.19 | [−1.84; 8.20] | 0.15 ± 0.10 | [−0.07; 0.38] |

Data are means ± SEM. *P < 0.05.

TABLE 3

Changes (mean ± SD) in lipid profiles (mmol/l) between baseline and the end of the maintenance treatment period.

| | MET | MET + REP | REP |
|---|---|---|---|
| Total cholesterol | 0.13 ± 0.13 | 0.13 ± 0.12 | 0.38 ± 0.12* |
| HDL cholesterol | 0.07 ± 0.03* | 0.05 ± 0.03 | 0.09 ± 0.03* |
| LDL cholesterol | 0.10 ± 0.12 | 0.11 ± 0.11 | 0.41 ± 0.12 |
| Triglycerides | −0.20 ± 0.17 | −0.10 ± 0.16 | 0.09 ± 0.16 |

*P < 0.05

Conclusions

Combination therapy with REP and MET provides better glycemic control than either REP or MET monotherapy in NIDDM patients who are inadequately controlled on metformin alone. Indeed, MET+REP treatment reduced $HbA_{1c}$ of this group of patients to the target value recommended by the American Diabetes Association (<7%).

What is claimed is:

1. A pharmaceutical composition comprising repaglinide and metformin together with a suitable carrier.

2. A pharmaceutical composition of claim 1 provided in the form of a tablet.

3. A pharmaceutical composition of claim 1 provided in the form of a capsule.

4. A method for treating non-insulin dependent diabetes mellitus (NIDDM) comprising administering to a patient in need of such treatment repaglinide in combination with metformin.

5. A kit for use in the treatment of a patient having non-insulin dependent diabetes mellitus (NIDDM), said kit comprising an amount of repaglinide formulated for administration to said patient and an amount of metformin formulated for administration to said patient.

* * * * *